(12) United States Patent
Kimber et al.

(10) Patent No.: US 6,565,529 B1
(45) Date of Patent: May 20, 2003

(54) TAMPER EVIDENT SYRINGE DESIGN

(75) Inventors: Michael Browning Kimber, New South Wales (AU); Frank Alexander Popovsky, New South Wales (AU)

(73) Assignee: Astra Pharmaceuticals PTR Ltd., New South Wales (AU)

( * ) Notice: Subject to any disclaimer, the term of this patent is extended or adjusted under 35 U.S.C. 154(b) by 0 days.

(21) Appl. No.: 09/051,989

(22) PCT Filed: Oct. 4, 1996

(86) PCT No.: PCT/AU96/00623

§ 371 (c)(1),
(2), (4) Date: Nov. 10, 1999

(87) PCT Pub. No.: WO91/12038

PCT Pub. Date: Aug. 22, 1991

(30) Foreign Application Priority Data

Oct. 24, 1995 (AU) .............................. PN6150

(51) Int. Cl.[7] .............................. A61M 5/00
(52) U.S. Cl. ...................... 604/110; 604/111
(58) Field of Search ................. 604/110, 111, 604/187, 218, 220, 222

(56) References Cited

U.S. PATENT DOCUMENTS

| | | | |
|---|---|---|---|
| 4,354,507 A | * 10/1982 | Raitto | 604/222 |
| 4,447,229 A | * 5/1984 | Botterfield | 604/111 |
| 4,571,242 A | 2/1986 | Klein et al. | |
| 4,832,695 A | 5/1989 | Rosenberg et al. | |
| 5,171,300 A | * 12/1992 | Blake, III et al. | 604/220 |
| 5,536,253 A | 7/1996 | Haber et al. | |
| 5,842,326 A | * 12/1998 | Wolf | 53/425 |

FOREIGN PATENT DOCUMENTS

| | | | | |
|---|---|---|---|---|
| AU | 90859/82 | | 3/1983 | |
| GB | 2117645 | | 10/1983 | |
| WO | 91/12038 | | 8/1991 | |
| WO | WO 95/00180 | * | 1/1995 | 53/425 |
| WO | 96/14100 | | 5/1996 | |

* cited by examiner

Primary Examiner—Manuel Mandez
(74) Attorney, Agent, or Firm—Vidas, Arrett & Steinkraus PA

(57) ABSTRACT

A plastic prefilled syringe (10) including a syringe body (11) and a plunger assembly (12), the syringe body (11) having opposed first (13) and second (14) ends and an inner wall (16) defining a cylindrical chamber (15) which contains an injectable solution (100), the first end (13) of the syringe body (11) being sealed by a closure and the second end (14) incorporating an opening (18), the plunger assembly (12) including a plunger shaft (22) extending through said opening (18) and a stopper (24) secured at an end of said shaft (22) within said chamber, the plunger assembly (12) being movable within the chamber with the stopper (24) being operable to seal the opening (18) wherein the plunger assembly (12) includes barrier means (26 and 29) on said shaft (22) the barrier means (26 and 29) being adapted, in conjunction with a part of the syringe body (16 and 19), to inhibit access to the injectable solution (100) through the opening (18).

14 Claims, 1 Drawing Sheet

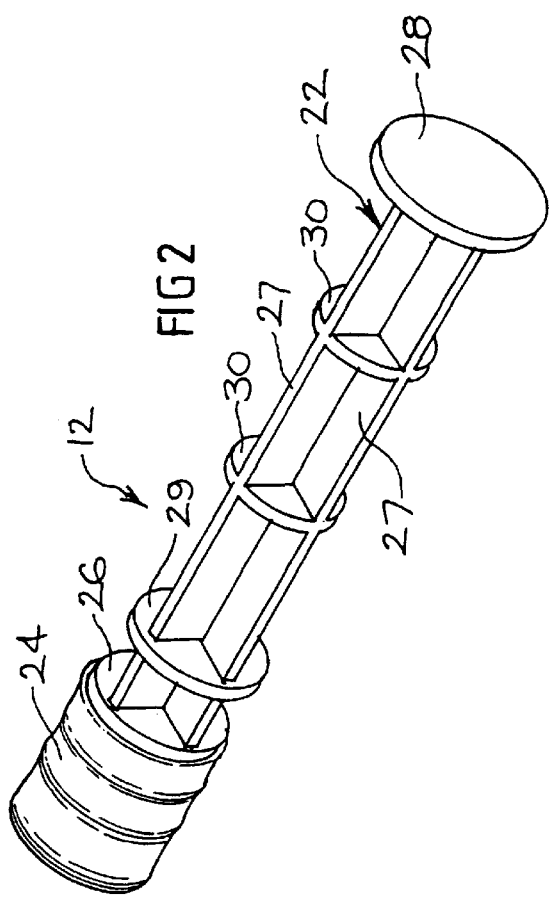
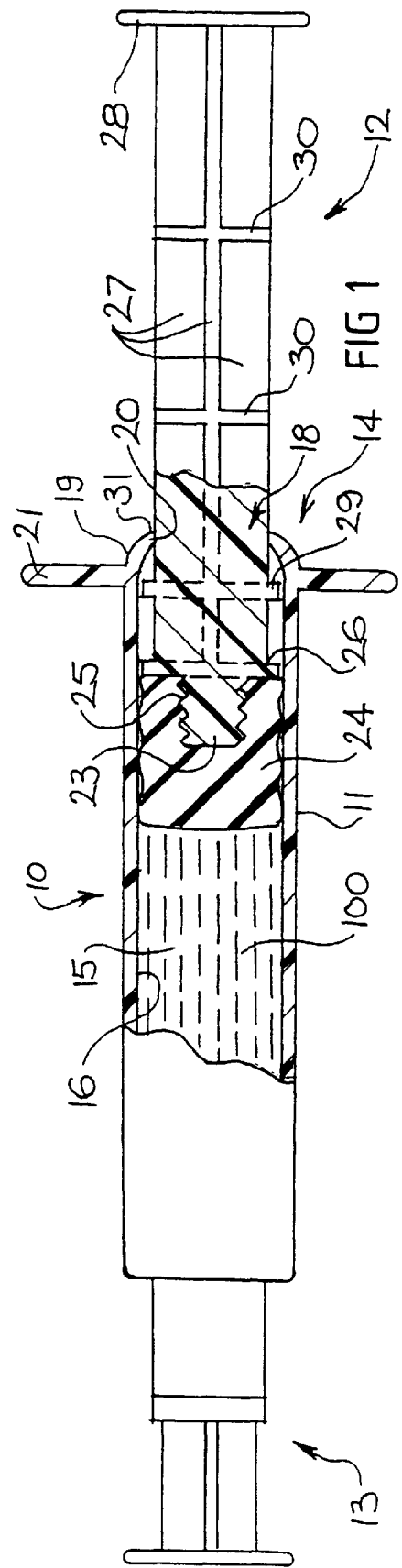

TAMPER EVIDENT SYRINGE DESIGN

INTRODUCTION

This invention relates to a syringe and in particular to a plastic syringe suitable for use as a prefilled product.

Prefilled plastic syringes are known. These syringes are disposable and are more convenient than disposable syringes which require filling before use as they come as a single dose product already accurately filled and labelled with the name of the injectable. These syringes are also safer as there is a lower risk of incorrect dosing on administration as well as a lower risk of transfer of transmissible viruses which may otherwise occur on transfer of the injectable from a separate ampoule.

PRIOR ART

Typically, prefilled syringes include a barrel containing an injectable solution and a plunger assembly. The barrel includes a closure at one end sealing an outlet opening and incorporates an opening at the other end in which the plunger assembly is located. The plunger assembly includes a stopper which seals the opening and further includes a plunger shaft which is connected to the stopper and which extends outwardly from the barrel. The syringe may also include an integral needle fitting at the closure end to provide a support for a hypodermic needle. The syringe may also incorporate other fittings, such as a luer lock finish to enable the syringe to be connected to other complementary fittings, such as those used with an intravenous drip. Examples of previous prefilled syringe designs are described in the applicant's earlier Australian Patents 595096 and 635631.

Being a prefilled product, it is important that the injectable be safely housed within the barrel. While previous prefilled syringes have maintained the injectable in an aseptic environment, the syringe has been susceptible to tampering after filling. Prefilled syringes are often used for the supply of narcotic substances intended to be delivered intravenously for therapeutic use. The supply of narcotic substances to hospitals, doctors and like persons is strictly controlled and such products are usually available only on prescription from a qualified medical practitioner. Organisations such as hospitals, control distribution carefully and generally narcotics are held in a cupboard or room to which there is limited access. Theft of narcotics is a major problem as there is a ready market of persons prepared to pay substantial premiums for restricted drugs.

An aim of the present invention is to provide a prefilled plastic syringe design which is more tamper resistant and tamper evident than previous designs.

SUMMARY OF THE INVENTION

According to the present invention, there is provided a plastic prefilled syringe including a syringe body and a plunger assembly, the syringe body having opposed first and second ends and an inner wall defining a cylindrical chamber which contains an injectable solution, the first end of the syringe body being sealed by a closure and the second end incorporating an opening, the plunger assembly including a plunger shaft extending through said opening and a stopper secured at an end of said shaft within said chamber, the plunger assembly being movable within the chamber with the stopper being operable to seal the opening wherein the plunger assembly includes barrier means on said shaft, the barrier means being adapted, in conjunction with a part of the syringe body, to inhibit access to the injectable solution through the opening.

DETAILED DESCRIPTION OF INVENTION

In one form, the barrier means is of substantially the same diameter as the cylindrical chamber of the syringe body and is thus adapted in conjunction with the inner wall of the chamber to restrict access to the injectable solution. In this embodiment of the invention, there is minimal clearance between the peripheral edge of the barrier means and the inner wall. This inhibits location of a conduit, such as a hypodermic needle along the interface between the stopper and the inner wall. Preferably in this arrangement, the barrier means is in spaced relationship to the stopper and the clearance between the barrier means and the inner wall is 0.3 mm or less. Most preferably it is between 0.1 to 0.3 mm.

In another form, the syringe body includes an annular abutment surface which extends inwardly from the inner wall at or adjacent the opening and the barrier means is adapted in conjunction with the abutment surface to restrict access to the injectable solution. In this embodiment of the invention the barrier means preferably extends outwardly from the shaft at a location intermediate the abutment surface and the stopper and is preferably in overlapping arrangement with the abutment surface so as to prevent removal of the plunger assembly from the syringe body. In this context and further in this specification the term "overlapping arrangement" is used to mean that the diameter of the barrier means is greater than the distance between opposite sides of the abutment surface. The overlapping arrangement inhibits a conduit such as a hypodermic needle being inserted into the injectable solution along the interface between the plunger assembly and the inner wall. A hypodermic needle is generally not flexible enough to bend about the abutment surface and the barrier means in a manner which would allow further movement of the head of the needle between the inner wall of the syringe and the stopper.

In a particularly preferred arrangement, the syringe is designed such that the barrier means is adapted to restrict access to the injectable solution in conjunction with both the abutment surface and the inner wall.

The applicant has realised that in previous syringe designs, the interface between the plunger assembly and the syringe body made the syringe susceptible to tampering as it was possible to locate a conduit, such as a hypodermic needle, along this interface into a position where the needle tip was in contact with the injectable solution. Once in this position, the injectable can be withdrawn through the needle and if desired, replaced by another solution such as a saline solution. Furthermore the needle could be withdrawn without marking the syringe body or plunger assembly to leave very little or no evidence of tamper.

An advantage of the preferred forms of the present invention is that the barrier means inhibits access to the injectable. In particular, the barrier means inhibits the insertion of a needle along the interface between the plunger assembly and the syringe body due to the minimal clearance between the barrier means and the inner wall and the overlapping arrangement between the abutment surface and barrier means. Furthermore, if an attempt is made to force the needle through the barrier means, then the needle is likely to be bent and/or become blocked thereby preventing withdrawal of the injectable. In addition any attempt to access the injectable by a needle is likely to mark the barrier means. Such marking provides evidence of tamper which is noticeable to an end user of the syringe and alerts them to the fact that the syringe has been tampered and that it should not be used. This improves the safety of the product and also assists in controlling distribution of the injectable solution.

Preferably the barrier means is in the form of a disc which extends about the shaft. Preferably the disc is integrally formed with the shaft during manufacture of the plunger assembly.

Preferably the syringe body includes a collar at the second end which defines an opening which is narrower than the diameter of the cylindrical chamber. In a preferred arrangement, the free end of the collar extends inwardly from the inner wall of the chamber to provide the above-mentioned abutment surface. Preferably in manufacture of the product, the free end of the collar is located in its inward extending position after placement of the plunger assembly within the chamber and typically, this is done by a thermo forming operation.

Preferably the stopper is connected to the end of the shaft. In one arrangement the stopper is mounted on a threaded stud formed at the end of the shaft. Preferably the stud is engagable within a recess formed in the stopper which incorporates a complementary threaded arrangement. Preferably the shaft also incorporates a disc adjacent the threaded stud which extends outwardly from the shaft and which is adapted to abut the stopper. The disc may form the barrier means. Alternatively in a preferred embodiment this disc with a second but spaced disc also located on the shaft and of similar size, together form the barrier means.

To minimise the material used in the manufacture of the shaft, it is preferable that the shaft is formed from a plurality of interconnected fins which extend outwardly from a central axis of the shaft. The fins are angularly spaced about the axis with their free ends defining the outer dimensions of the shaft. In a preferred arrangement, the shaft further includes at least one web which extends transverse to the shaft axis and which interconnects adjacent fins. Preferably these webs extend substantially to the free end of the respective fins. The advantage of this arrangement is that these webs further inhibit the placement of a needle along the interface between the plunger assembly and the syringe body and thereby further improve the tamper resistance of the syringe.

Preferably the syringe of this invention is made from elastomer such as polypropylene, polyethylene or polyethylene terephthalate. Most preferably, it is injection molded from polypropylene.

It is convenient to hereinafter describe an embodiment of the invention in greater detail with reference to the accompanying drawings. The particularity of these drawings in the related description is not to be understood as superseding the generality of the preceding broad description of the invention.

In the drawings:

FIG. 1 is a fragmented sectional view of a prefilled syringe; and

FIG. 2 is a perspective view of a plunger assembly for use in the syringe of FIG. 1.

In the drawings, a syringe 10 is illustrated which comprises a syringe body 11 and plunger assembly 12.

The syringe body 11 has opposing ends (13, 14) and incorporates a cylindrical chamber 15 which is defined by an inner wall 16 of the body 11. The chamber extends between the ends 13 and 14 and is arranged in use to contain an injectable solution 100.

At one end 13 of the syringe body 11, a closure is formed whereas the other end 14 incorporates an opening 18. In the illustrated arrangement, the opening is defined by a collar 19 which incorporates a free end 20 which extends inwardly from the cylinder wall 16. In this way, the opening 18 is constricted as compared to the chamber bore. Finger grips 21 project outwardly from the body 11.

The plunger assembly 12 extends through the opening 18. The assembly 12 includes a shaft 22 which incorporates a threaded stud 23 at one end on which a stopper 24 is connected. The stopper includes a recess 25 which incorporates a complementary thread to interconnect the stopper to the stud. An abutment disc 26 extends outwardly from the shaft 22 adjacent the stud 23 and is adapted to abut the stopper 24. The stopper is located within the chamber 15 and is adapted to seal the opening 18.

The shaft 22 is formed from radial fins 27 which extend outwardly from an axis of the shaft. A thumb rest 28 is located at the outer end of the shaft 22 and is adapted to facilitate the application of pressure on the shaft to move the plunger assembly 12 along the chamber 15.

A disc 29 is formed on the shaft and extends radially outwardly beyond the fins 27. The disc 29 extends continuously around the shaft and is adapted to be located within the chamber 15 in spaced relationship to the stopper 24. In a typical arrangement the disc 29 is spaced from the disc 26 by approximately 3 mm.

Two smaller webs 30 are also located on the shaft in between the disc 29 and the thumb rest 28. The smaller webs interconnect each of the adjacent fins 27 but only extend to the respective outer edges of the fins.

The disc 29 and the disc 26 are approximately the same size and are dimensioned such that there is only minimal clearance between these members and the inner wall 16 of the body 12. In the illustrated arrangement this clearance is approximately 0.2 mm. Furthermore the disc 29 is adapted to prevent removal of the plunger assembly 12 from the chamber 15 through engaging an inner abutment surface 31 of the collar.

With the arrangement as illustrated, the syringe 10 is adapted such that access to the solution 100 contained in the chamber through the opening 18 is inhibited. In particular the syringe 10 is arranged such that it is very difficult to insert a hypodermic needle along the interface between the plunger assembly 12 and the syringe body 11 due to the minimal clearance between the discs 26 and 29 and the inner wall 16 and also because the free end 20 of the collar 19 overlaps the disc 29. Further positioning of a needle to gain access to the solution 100 is inhibited by the smaller webs 30 located on the shaft 22.

It will be appreciated having regard to the foregoing example of a preferred embodiment, that the present invention provides significant tamper resistance at the interface between the syringe body and the plunger assembly.

Finally, it is to be understood that various alterations, modifications and/or additions may be introduced into the construction and arrangement of the parts previously described without departing from the spirit or ambit of the invention.

What is claimed is:

1. A plastic prefilled syringe including a syringe body and a plunger assembly, the syringe body having opposed first and second ends and an inner wall defining a cylindrical chamber which contains an injectable solution, the first end of the syringe body being sealed by a closure and the second end incorporating an opening, the plunger assembly including a plunger shaft extending through said opening and a stopper secured at an end of said shaft within said chamber, the plunger assembly being movable within the chamber with the stopper sealing the injectable solution from the opening, wherein the plunger assembly includes barrier means on the shaft which has a diameter greater than the opening and the syringe body includes an integral collar at or adjacent the second end which extends inwardly of the inner wall of the chamber such that the barrier means, in conjunction with the integral collar, inhibits access to the injectable solution through the opening.

2. A syringe according to claim 1, wherein said barrier means is in the form of a disc extending around said shaft.

3. A syringe according to claim 1, wherein the barrier means is located within the chamber and is adapted to restrict access to the injectable solution in conjunction with the inner wall of the syringe body.

4. A syringe according to claim 3, wherein the barrier means is sized such that there is a clearance of between 0.1 to 0.3 mm between said barrier means and said inner wall.

5. A syringe according to claim 4, wherein the barrier means is sized such that there is a clearance of approximately 0.2 mm between said barrier means and said inner wall.

6. A syringe according to claim 1, wherein the syringe body includes an annular abutment surface which extends inwardly from the inner wall at or adjacent the opening and the barrier means on the plunger assembly extends outwardly from the shaft at a location intermediate the annular abutment surface and the stopper so as to be engagable with said abutment surface.

7. A syringe according to claim 1, wherein the integral collar includes an annular abutment surface which is located inwardly of the inner wall at or adjacent the opening and the barrier means on the plunger assembly extends outwardly from the shaft so as to be contactable against said abutment surface so to prevent withdrawal of the plunger through the said opening.

8. A syringe according to claim 7, wherein said free end of said collar is formed in its inwardly extending position after placement of said plunger assembly within said chamber.

9. A syringe according to claim 8, wherein the free end of the collar is formed into its inwardly extending position by a thermo forming operation.

10. A syringe according to claim 1, wherein said barrier means includes a disc adjacent said stopper which extends outwardly from said shaft and which is adapted to abut said stopper.

11. A syringe according to claim 1, wherein said barrier means includes a disc adjacent said stopper which extends outwardly from said shaft and which abuts against said stopper.

12. A syringe according to claim 1, wherein the shaft includes a plurality of fins extending outwardly from a central axis of the shaft, the fins being angularly spaced about said shaft with the free ends of said fins defining the outer dimensions of said shaft, and wherein said shaft further includes at least one web extending transverse to said shaft axis and interconnecting adjacent fins.

13. A syringe according to claim 1 wherein the shaft includes a plurality of fins extending outwardly from a central axis of the shaft, the fins being angularly spaced about said shaft with the free ends of said fins defining the outer dimensions of said shaft, and wherein said shaft further includes at least one web extending transverse to said shaft axis and interconnecting adjacent fins.

14. A syringe according to claim 13 wherein each web extends substantially to the free end of said respective fins.

* * * * *

UNITED STATES PATENT AND TRADEMARK OFFICE
CERTIFICATE OF CORRECTION

| | | |
|---|---|---|
| PATENT NO. | : 6,565,529 B1 | Page 1 of 1 |
| APPLICATION NO. | : 09/051989 | |
| DATED | : May 20, 2003 | |
| INVENTOR(S) | : Michael Browning Kimber and Frank Alexander Popovsky | |

It is certified that error appears in the above-identified patent and that said Letters Patent is hereby corrected as shown below:

On the face of the patent, at (87) – the PCT Pub. Date should be corrected to read:

May 1, 1997

Signed and Sealed this

Twentieth Day of February, 2007

JON W. DUDAS
*Director of the United States Patent and Trademark Office*